United States Patent
Geissler et al.

(10) Patent No.: US 7,455,683 B2
(45) Date of Patent: Nov. 25, 2008

(54) METHODS AND DEVICES FOR REPAIRING TRIANGULAR FIBROCARTILAGE COMPLEX TEARS

(75) Inventors: William Geissler, Brandon, MS (US); Shelby Cook, Mansfield, MA (US); Meghan Scanlon, Waltham, MA (US); Donna Belloli, Mansfield, MA (US)

(73) Assignee: DePuy Mitek, Inc., Raynham, MA (US)

( * ) Notice: Subject to any disclaimer, the term of this patent is extended or adjusted under 35 U.S.C. 154(b) by 979 days.

(21) Appl. No.: 10/708,360

(22) Filed: Feb. 26, 2004

(65) Prior Publication Data
US 2005/0192632 A1 Sep. 1, 2005

(51) Int. Cl.
*A61B 17/04* (2006.01)

(52) U.S. Cl. .................... 606/232; 606/60; 606/233

(58) Field of Classification Search ................ 606/60, 606/232, 233
See application file for complete search history.

(56) References Cited

U.S. PATENT DOCUMENTS

| | | | |
|---|---|---|---|
| 2,751,907 A | 6/1956 | Hickey | |
| 3,308,822 A | 3/1967 | DeLuca | |
| 3,745,590 A * | 7/1973 | Stubstad | 623/13.1 |
| 4,586,926 A | 5/1986 | Osborne | |
| 4,666,438 A | 5/1987 | Raulerson | |
| 4,741,330 A | 5/1988 | Hayhurst | |
| 5,085,661 A | 2/1992 | Moss | |
| RE34,021 E | 8/1992 | Mueller et al. | |
| 5,269,809 A | 12/1993 | Hayhurst | |
| 5,290,267 A | 3/1994 | Zimmermann | |
| 5,464,424 A | 11/1995 | O'Donnell, Jr. | |
| 5,484,422 A | 1/1996 | Sloane, Jr. et al. | |
| 5,500,000 A | 3/1996 | Feagin et al. | |
| 5,536,259 A | 7/1996 | Utterberg | |
| 5,575,780 A | 11/1996 | Saito | |
| 5,601,571 A | 2/1997 | Moss | |
| 5,618,314 A | 4/1997 | Harwin et al. | |
| 5,626,614 A | 5/1997 | Hart | |
| 5,630,824 A | 5/1997 | Hart | |
| 5,647,874 A | 7/1997 | Hayhurst | |
| 5,810,788 A | 9/1998 | Racz | |
| 5,817,074 A | 10/1998 | Racz | |
| 5,921,986 A * | 7/1999 | Bonutti | 606/60 |
| 5,941,439 A | 8/1999 | Kammerer et al. | |
| 5,954,747 A | 9/1999 | Clark | |

(Continued)

OTHER PUBLICATIONS

Stuart E. Fromm, M.D., RapidLoc Meniscal Repair System, Surgical Technique for Repair of Meniscal Tears, Mitek Products, Jul. 2001.

*Primary Examiner*—Michael J. Hayes
*Assistant Examiner*—Michael G. Mendoza
(74) *Attorney, Agent, or Firm*—Nutter, McClennen & Fish LLP

(57) ABSTRACT

Methods and devices for repairing the TFCC of a patient's wrist are provided. In general, the device includes first and second anchor bodies that are connected to one another by a suture. The first anchor body is configured to be passed through a portion of the TFCC of a patient's wrist and an anchoring tissue, preferably using a delivery device, such that the first anchor body is positioned across a torn portion of the TFCC, the second anchor body is positioned across the anchoring tissue, and the suture extends therebetween. The suture can then be tensioned to anchor the TFCC to the anchoring tissue.

27 Claims, 7 Drawing Sheets

U.S. PATENT DOCUMENTS

| | | |
|---|---|---|
| 5,968,022 A | 10/1999 | Saito |
| 6,099,568 A | 8/2000 | Simoniam et al. |
| 6,110,207 A | 8/2000 | Eichhorn et al. |
| 6,213,989 B1 | 4/2001 | Utterberg |
| 6,293,961 B2 | 9/2001 | Schwartz et al. |
| 6,302,915 B1 | 10/2001 | Cooney, III et al. |
| 6,306,159 B1 | 10/2001 | Schwartz et al. |
| 6,319,271 B1 | 11/2001 | Schwartz et al. |
| 6,432,123 B2 | 8/2002 | Schwartz et al. |
| 6,712,830 B2 * | 3/2004 | Esplin ........................ 606/152 |
| 2001/0008971 A1 | 7/2001 | Schwartz et al. |
| 2001/0041916 A1 | 11/2001 | Bonutti |
| 2001/0051816 A1 | 12/2001 | Enzerink et al. |
| 2002/0169478 A1 | 11/2002 | Schwartz et al. |
| 2003/0120276 A1 | 6/2003 | Tallarida et al. |

* cited by examiner

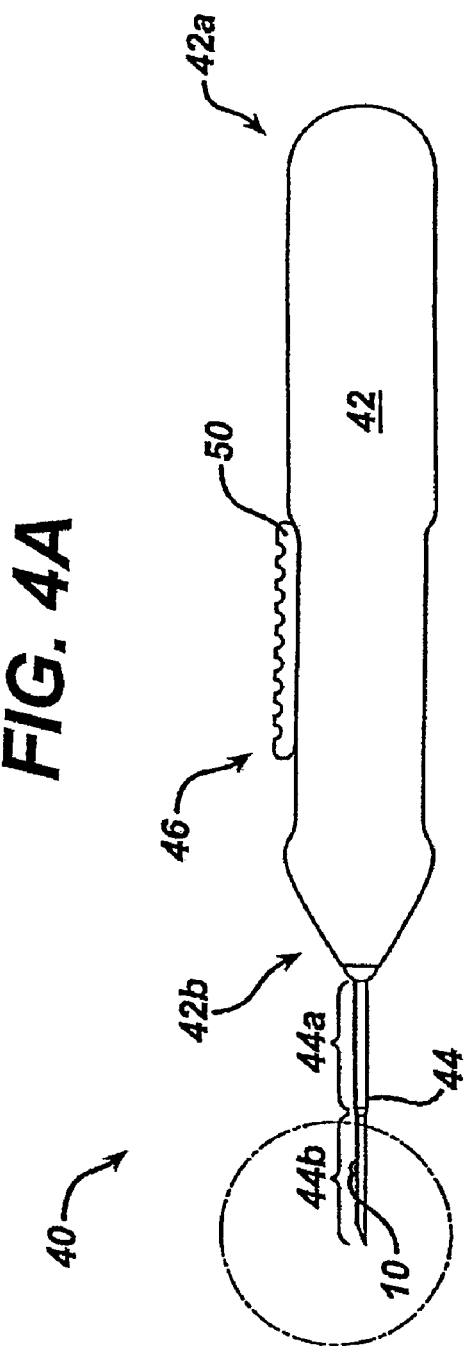

METHODS AND DEVICES FOR REPAIRING TRIANGULAR FIBROCARTILAGE COMPLEX TEARS

FIELD OF THE INVENTION

The present invention relates to methods and devices for repairing tears in the triangular fibrocartilage complex of a patient's wrist.

BACKGROUND OF THE INVENTION

The triangular fibrocartilage complex (TFCC) of a human wrist is quite complicated. It includes the articular disc, meniscus homologue, both the volar and dorsal radioulnar ligaments, and the tendon sheath of the extensor carpi ulnaris tendon. The disc portion of the triangular fibrocartilage complex has thickening of its volar and dorsal margins, which are known as the volar and dorsal radioulnar ligaments. These ligaments function as important stabilizers to the distal radioulnar joint. Approximately 20 percent of the load of the forearm is transferred through the ulna side of the wrist and the triangular fibrocartilage complex. The triangular fibrocartilage complex also acts as an extension of the articular surface of the radius to support the proximal carpal row.

Tears or lesions to the TFCC result in chronic pain and wrist instability. Currently, the TFCC can be repaired using a mattress stitch to place several sutures across the lesion, either using open surgery or arthroscopic surgery, to re-approximate the tear. This technique requires complicated suture management, as well as extensive knowledge of the anatomy of the wrist by the surgeon. In fact, due to the complicated nature of the procedure, many TFCC tears go untreated and undiagnosed.

Accordingly, there remains a need for improved methods and devices for repairing the TFCC of a patient's wrist.

BRIEF SUMMARY OF THE INVENTION

The present invention generally provides a method for repairing tears in the triangular fibrocartilage complex of a patient's wrist. In one embodiment, a delivery device carrying a first anchor body that is connected to a second anchor body by a suture is passed through an anchoring tissue and a portion of the triangular fibrocartilage complex of a patient's wrist. The first anchor body is then released from the delivery device such that the first anchor body is positioned across a torn portion of the triangular fibrocartilage complex, the second anchor body is positioned across an anchoring tissue, and the suture extends therebetween. The suture can then be tensioned to anchor the triangular fibrocartilage complex to the anchoring tissue. In an exemplary embodiment, the suture preferably includes a slip knot formed thereon, and the step of tensioning the suture comprises pulling a trailing end of the suture such that the slip knot and the second anchor body move toward the first anchor body.

The first and second anchor bodies can have a variety of configurations. Preferably, however, each anchor body includes a central portion that is adapted to receive the suture, and a tissue-engaging portion. A bore can extend through the central portion for receiving the suture. In an exemplary embodiment, the central portion of the first anchor body has a substantially semi-circular, planar shape, and the tissue-engaging portion has a generally elongate, somewhat cylindrical shape. More preferably, the tissue-engaging portion has a length that is greater than a maximum diameter of the central portion such that opposed ends of the tissue-engaging portion form tissue-engaging wings. The tissue-engaging portion can also have a length that is greater than a height of the central portion. The second anchor body can also have a variety of configurations, but in an exemplary embodiment the tissue-engaging portion of the second anchor body is in the form of a circular base, and the central portion comprises a substantially cylindrical extension of the circular base with chamfered sidewalls. A diameter of the circular base is preferably greater than a maximum diameter of the substantially cylindrical extension. The second anchor body also preferably includes a suture-receiving bore extending through the circular base and the substantially cylindrical extension. A recess can optionally be formed in an opening of the suture-receiving bore in the circular base for seating a knot formed on the suture.

The configuration of the delivery device can also vary, but in one embodiment it includes an elongate needle having a channel formed in at least a distal portion thereof and adapted to slidably receive at least a portion of the first anchor body, and more preferably that is adapted to slidably receive a tissue-engaging portion of the first anchor body. The delivery device also preferably includes a handle member coupled to the elongate needle, and a trigger mechanism formed on the handle and effective to, upon actuation, advance the first anchor body in a distal direction to release the first anchor body. A suture-receiving channel can be formed in the handle member to seat a trailing portion of the suture.

The present invention also provides an anchor system for repairing tears in the triangular fibrocartilage complex. The system preferably includes a first anchor body having a central portion adapted to receive a suture, and opposed wing members extending from opposed sides of the central portion. The wing members preferably define a length that is greater than a height of the central portion. The system also includes a second anchor body having a circular base with a substantially cylindrical central portion extending therefrom. A bore preferably extends through the circular base and the substantially cylindrical central portion for receiving a suture. The system further includes a suture loop that extends through the central portion of the first and second anchor bodies, and that includes a slip knot formed thereon and positioned adjacent the second anchor body. While the system can be used to repair a variety of soft tissue tears, the first and second anchor bodies each preferably have a size that is adapted to be used to repair tears in the triangular fibrocartilage complex of a patient's wrist.

BRIEF DESCRIPTION OF THE DRAWINGS

The invention will be more fully understood from the following detailed description taken in conjunction with the accompanying drawings, in which:

FIG. 4A is a side view of one embodiment of a delivery device in accordance with the present invention;

DETAILED DESCRIPTION OF THE INVENTION

The present invention generally provides methods and devices for repairing the TFCC of a patient's wrist. In general, the device includes first and second anchor bodies that are connected to one another by a suture. The first anchor body is configured to be passed through a torn portion of the TFCC of a patient's wrist and an anchoring tissue, preferably using a delivery device, such that the first anchor body is positioned across a torn portion of the TFCC, the second anchor body is positioned across the anchoring tissue, and the suture extends therebetween. The suture can then be tensioned to re-approximate the torn TFCC toward the anchoring tissue and thereby secure it to the anchoring tissue.

The methods and devices of the present invention offer several advantages over prior art suturing techniques. In particular, the methods and devices of the present invention can be used arthroscopically to simply, safely, rapidly, and effectively repair both radial and ulna-sided tears to the TFCC. Several devices can easily be implanted to re-approximate the torn tissue, and the suture can be tensioned and secured without the need for extensive suture management.

FIGS. 1A-2B illustrate an exemplary embodiment of first and second anchor bodies 10, 20 of a device in accordance with the present invention. While each anchor body 10, 20 can have a variety of configurations, the anchor bodies 10, 20 should be effective to allow torn tissue to be re-approximated and securely attached to anchoring tissue, thus allowing the torn tissue to be repaired. Each anchor body 10, 20 can also be formed from a variety of materials, but in an exemplary embodiment they are formed from a bioabsorbable polymeric material. Suitable materials include, for example, a bioabsorbable polylactic acid (PLA).

Figure 1A:
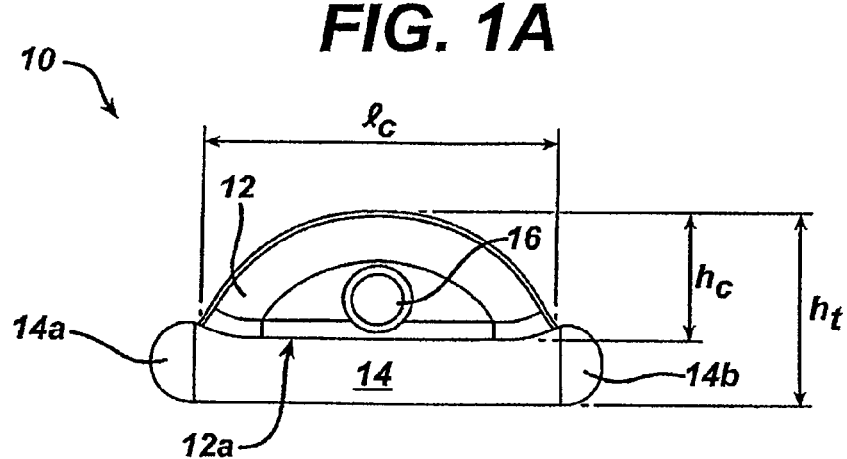
FIG. 1A is a side view of one embodiment of a first anchor body in accordance with the present invention.
Figure 1B:
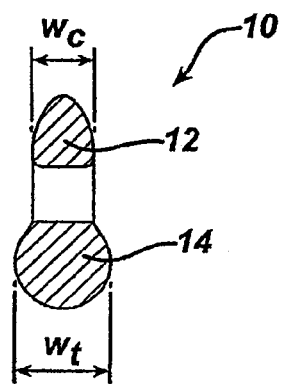
FIG. 1B is an end view of the first anchor body shown in FIG. 1A.
Figure 1C:
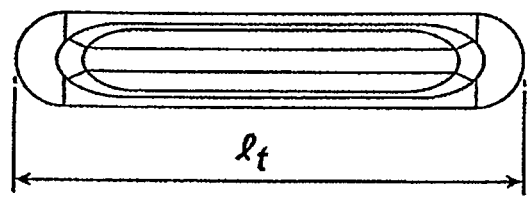
FIG. 1C is a bottom view of the first anchor body shown in FIG. 1A.

FIGS. 1A-1C illustrate the first anchor body 10, which generally includes a central portion 12 that is adapted to receive suture, and a tissue-engaging portion 14 that is adapted to engage tissue. The central portion 12 preferably has a generally semi-circular shape, and it can include a suture-receiving member formed thereon. While the suture-receiving member can have any configuration, and it can be formed anywhere on the first anchor body 10, FIG. 1A illustrates a bore 16 extending through the central portion 12 at a substantial mid-point thereof. The bore 16 allows a suture to be positioned therethrough, allowing a suture loop to be formed to attach the first anchor body 10 to the second anchor body 20, as will be discussed in more detail below. The tissue-engaging portion 14 can also have a variety of shapes and sizes, but it preferably has a substantially elongate, cylindrical shape. Such a shape allows the tissue-engaging portion 14 of the first anchor body 10 to be slidably positioned within a delivery device, as will be discussed in more detail with respect to FIGS. 4A-4B. The tissue-engaging portion 14 can be mated to or integrally formed with the planar side 12a of the central portion 12, such that the central portion 12 extends outward from the tissue-engaging portion 14. The tissue-engaging portion 14 also preferably has a length $l_t$ that is greater than a maximum length l of the central portion 12, such that opposed ends 14a, 14b of the tissue-engaging portion 14 form tissue-engaging wings. The wings 14a, 14b provide an enlarged surface area that facilitates engagement with the tissue, thus preventing the first anchor body 10 from being pulled through the tissue. The length l of the tissue-engaging portion 14 can also be greater than the height h of the central portion 12, and the width w of the tissue-engaging portion 14 can be greater than a width w of the central portion 14, thus providing the first anchor body 10 with a relatively small profile. This is particularly advantageous since the device is used to repair the TFCC, which requires implants that are very small in size.

While the size of the first anchor body 10 can vary, in an exemplary embodiment the first anchor body 10 has a height $h_1$ that is in the range of about 0.75 mm to 1.25 mm, and more preferably that is about 1.00 mm, a length l that is in the range of about 3.5 mm to 4.5 mm, and more preferably that is about 4.0 mm, a maximum width, i.e., with width w of the tissue-engaging portion 14, that is in the range of about 0.5 mm to 1.5 mm, and more preferably that is about 0.75 mm, and a minimum width, i.e., the width w of the central portion 12, that is in the range of about 0.25 mm to 1.5 mm, and more preferably that is about 0.50 mm. The central portion 12 of the first anchor body 10 also preferably has a maximum length, i.e., the length l of the central portion 12, that is in the range of about 2.0 mm to 4.0 mm, and more preferably that is about 3.0 mm.

Figure 2A:
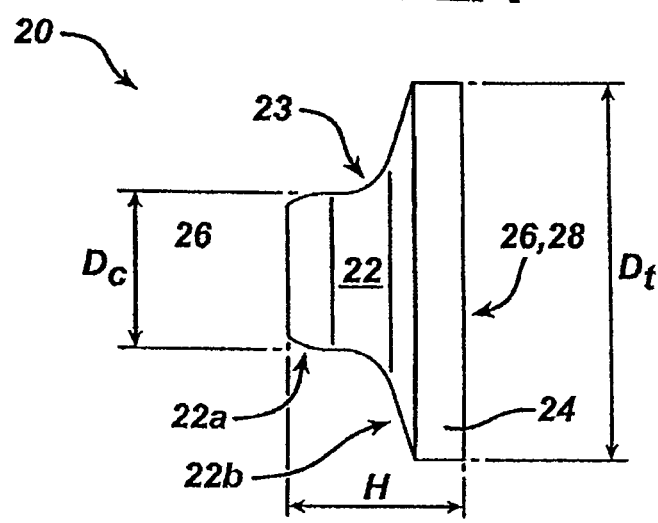
FIG. 2A is a side view of one embodiment of a second anchor body in accordance with the present invention.
Figure 2B:
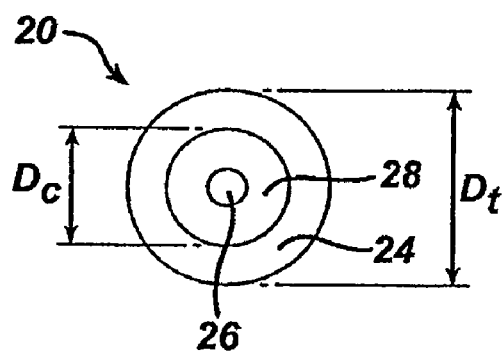
FIG. 2B is a bottom view of the second anchor body of FIG. 2A.
Figure 2C:
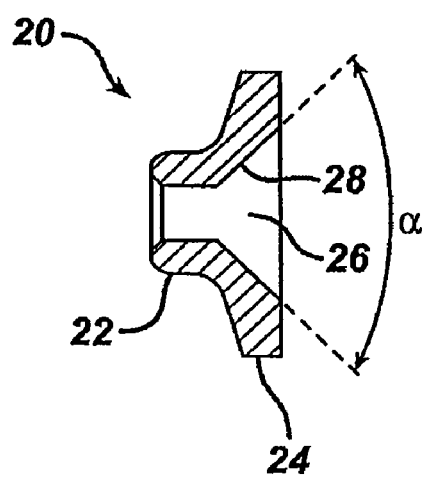
FIG. 2C illustrates a cross-sectional view of the second anchor body show in FIG. 2A.

FIGS. 2A-2C illustrate an exemplary embodiment of the second anchor body 20, which is preferably coupled to the first anchor body 10 by a suture when the device is in use, as will be described in more detail below. While the second anchor body 20 can have a variety of configurations, it also preferably includes a central portion 22 that is adapted to receive suture, and a tissue-engaging portion 24 that is adapted to engage tissue. Unlike the first anchor body 10, however, the central portion 22 preferably has a somewhat cylindrical shape that defines a suture-receiving bore 26 extending therethrough for receiving suture. The cylindrical shape of the central portion 22 is preferably constant between opposed ends 22a, 22b thereof. However, the second anchor body 20 can include chamfered sidewalls, as shown in FIGS. 2A and 2C, such that the central portion 22 includes a transition zone 23 formed between the central portion 22 and the tissue-engaging portion 24. In an exemplary embodiment, the transition zone 23 is relatively small such that the diameter $D_c$ of the central portion 22 remains substantially constant between first and second opposed ends 22a, 22b of the central portion. The diameter D increases significantly at the second end 22b adjacent to the tissue-engaging portion 24 to connected to the tissue-engaging portion 24. Such a configuration allows the thickness of the central portion 22 to be substantially uniform throughout, providing structural integrity to the second anchor body 20. This is particularly desirable, as the anchor body 20 needs to be relatively small to allow it to be used to repair the TFCC of a patient's wrist. The cylindrical shape of the central portion 22 also allows the central portion 22 to extend into or sit within at least a portion of an opening of a bone hole or a hole formed through tissue, as will be discussed in more detail below.

The tissue-engaging portion 24, which can be fixedly attached to or integrally formed with the central portion 22, is preferably in the form of a circular base that extends radially outward from one end of the central portion 22. In other words, the central portion 22 is a cylindrical extension of, or a flange formed on, the circular base that forms the tissue-engaging portion 24. The diameter $D_t$ of the circular base of the tissue-engaging portion 24 can vary, but it is preferably greater than a maximum diameter D of the substantially cylindrical extension that forms the central portion 22. The diameter D of the tissue-engaging portion 24 should at least be sufficient to allow the tissue-engaging portion 24 to engage tissue.

The second anchor body 20 can also include a recess 28 that is adapted to seat a knot formed on the suture. While the recess 28 can be formed anywhere on the anchor body 20, it is preferably formed within the opening of the suture-receiving bore 26, as shown in FIG. 2B. The shape of the recess 28 can vary, but it should allow a knot in the suture to sit sub-flush with the central portion 22, and more preferably it should have a size that does not interfere with the structural integrity of the second anchor body 20. In an exemplary embodiment, the recess 28 is chamfered such that opposed sides of the inner sidewall that forms the recess 28 are positioned at an angle with respect to one another. While the angle can vary, in the illustrated embodiment the opposed sides of the inner sidewall that forms recess 28 are positioned at a 90° angle with respect to one another. This allows the suture knot to fit securely within the recess 28, yet it does not interfere with the structural integrity of the implant 20.

While the size of the second anchor body 20 can vary, in an exemplary embodiment the second anchor body 20 has a height H that is in the range of about 1.0 mm to 1.5 mm, and more preferably that is about 1.3 mm, a maximum outer diameter, i.e., the diameter D of the tissue-engaging portion 24, that is in the range of about 3.0 mm to 4.0 mm, and more preferably that is about 3.5 mm, and a minimum outer diameter, i.e., the diameter D of central portion 22, that is in the range of about 0.75 mm to 1.25 mm, and more preferably that is about 1.0 mm.

In use, the first and second anchor bodies 10, 20 are connected to one another by a suture that allows the first and second anchor bodies 10, 20 to be positioned on opposed sides of an anchoring tissue and the torn tissue being repaired, such that the torn tissue can be pulled toward the anchoring tissue using the suture to re-approximate the tear. While virtually any type of suture can be used, the suture is preferably a non-absorbable suture that is effective to allow the torn tissue to be securely re-attached. By way of non-limiting example, an exemplary suture for use with the present invention is Ethibond® manufactured by Ethicon, Inc., a Johnson & Johnson company.

The suture can be coupled to the first and second anchor bodies using various techniques known in the art, but in an exemplary embodiment a slip knot is used to attach the suture to the first and second anchor bodies. A slip knot will allow the second anchor body to slidably move along the suture with respect to the first anchor body, thus allowing the torn tissue to be re-approximated toward the anchoring tissue, thereby closing the tear. A slip knot will also lock the anchor bodies 10, 20 in position with respect to one another when the device is implanted, thus eliminating the need to tie the suture. Techniques for forming slip knots are known in the art, and a variety of techniques can be used.

Figure 3:
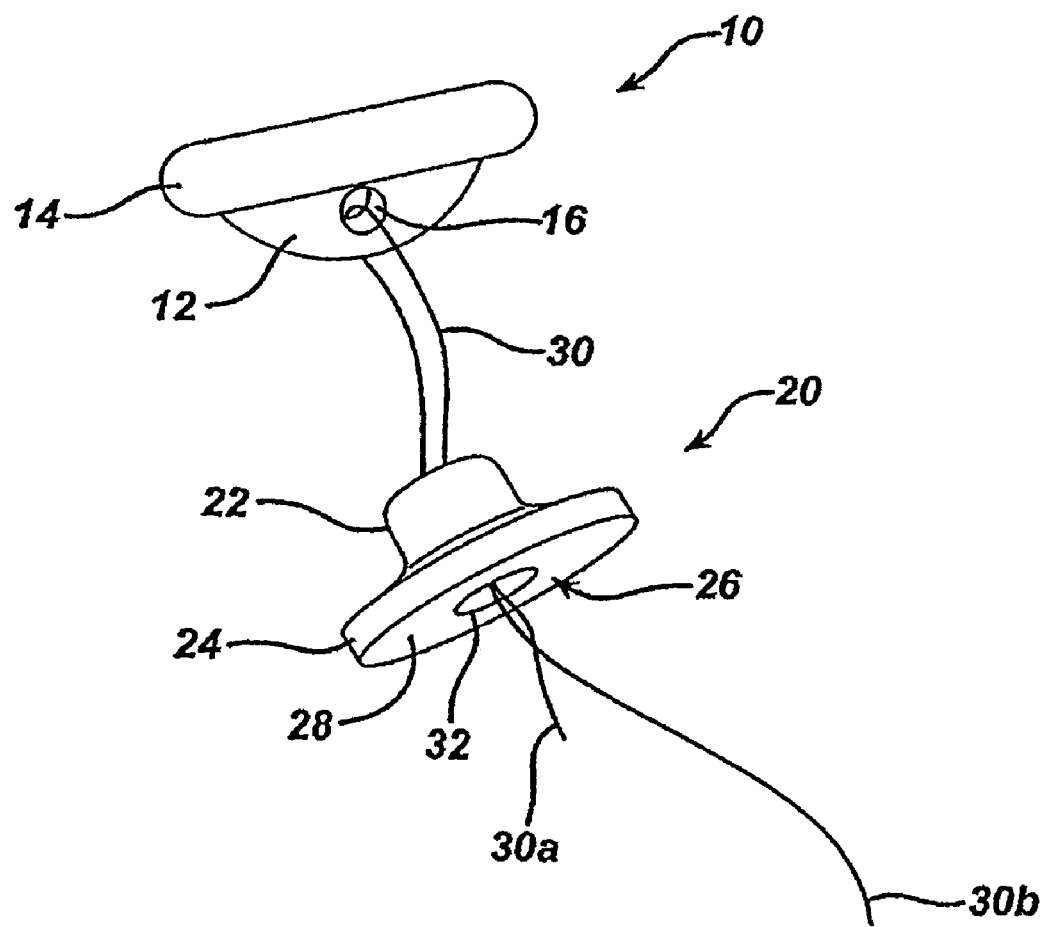
FIG. 3 is an illustration of the first and second anchor bodies shown in FIGS. 1A-2B attached to one another by a suture.

FIG. 3 illustrates the first and second anchor bodies 10, 20 coupled to one another by a suture 30. As shown, the suture 30 is passed through the bore 16 in the central portion 12 of the first anchor body 10 to form a suture loop. The two free ends 30a, 30b of the suture 30 are passed through the suture-receiving bore 26 in the second anchor body 20, and a slip knot 32 is formed to allow the second anchor body 20 to be slidably moved along the suture 30 with respect to the first anchor body 10. As shown, the slip knot 32 is positioned with the suture-receiving recess 28 in the tissue-engaging portion 24 of the second anchor body 20. A free end 30b of the suture 30 extends from the slip knot 32 and it can be used to tension the suture 30, thereby decreasing the size of the loop between the first and second anchor bodies 10, 20 to bring the bodies 10, 20 toward one another.

A variety of techniques can be used to implant the first and second anchor bodies 10, 20, however in an exemplary embodiment, a delivery device is used to implant the first and second anchor bodies 10, 20. The configuration of the delivery device can vary, but it should effective to insert the first anchor body 10 through tissue, and then to release the first anchor body 10. FIG. 4A illustrates an exemplary embodiment of a delivery device 40. As shown, the device 40 generally includes a handle member 42 having an elongate needle 44 extending distally therefrom. The needle 44 is adapted to slidably retain the first anchor body 10, and the handle 42 includes a trigger mechanism 46 formed thereon that is effective to cause the first anchor body 10 to be released from the needle 44 when the trigger 46 is actuated. The second anchor body 20 can remain disposed on the suture which extends from the first anchor body 10. The second anchor body 20 does not need not to be loaded onto the delivery device 40. However, a person skilled in the art will appreciate that the delivery device can optionally be adapted to retain the second anchor body 20 in combination with the first anchor body 10, or alternatively to the first anchor body 10.

The elongate needle 44 can have a variety of configurations, shapes, and sizes, but in general it preferably has a size that is adapted for use in arthroscopic surgery to repair a torn TFCC. More particularly, the needle 44 is preferably at least a 16 gauge needle. The distal-most portion 44b of the needle 44 can, however, be smaller in diameter than the proximal portion 44a of the needle 44, and in particular the distal-most portion 44b of the needle 44 is preferably an 18 gauge needle. The shape of the needle 44 can also vary, and it can be substantially straight, or it can include one or more bends formed therein depending on the particular type of repair being performed. In one embodiment, the distal-most portion 44b of the needle 44 is positioned at an angle (not shown) with respect to the proximal portion 44a of the needle 44 to facilitate insertion of the first anchor body 10 through tissue.

Figure 4B:
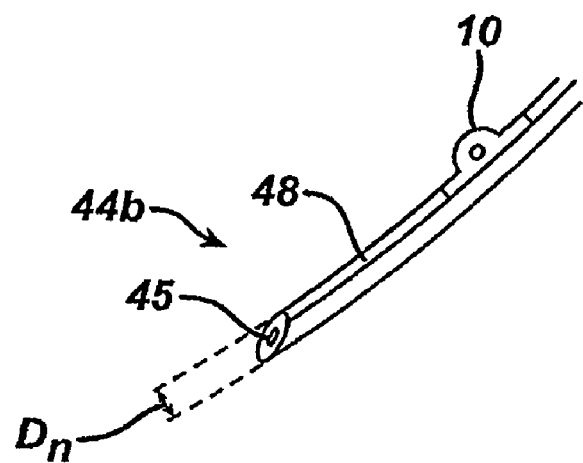
FIG. 4B is a perspective view of the distal end of the elongate needle of the delivery device shown in FIG. 4A.

As stated above, the needle 44 is adapted to slidably receive at least a portion of the first anchor body 10, as shown. While a variety of techniques can be used, the needle 44 preferably includes a channel 48 formed in at least a distal portion 44b thereof and in communication with the inner lumen 45 of the needle 44, as shown in FIG. 4B. In an exemplary embodiment, the channel 48 is configured to receive the central portion 12 of the first anchor body 10 to allow the tissue-engaging portion 14 to be slidably disposed within the inner lumen 45 of the needle 44. The remainder of the first anchor body 10, i.e., the central portion 12, can extend from the tissue-engaging portion 14 and protrude outward through the channel 48. The elongate needle 44 also preferably has an outer diameter $D_n$, shown in FIG. 4B, that is substantially the same as or greater than an outer diameter D of the cylindrical central portion 22 of the second anchor body 20. This will allow the central portion 22 of the second anchor body 20 to sit within the bore that is formed through the tissue through which the elongate needle 44 is inserted, thus allowing the tissue-engaging portion 24 of the second anchor body 20 to rest against and engage the tissue.

The handle member 42 of the delivery device 40 can also have a variety of configurations, but it should allow the device 40 to be easily grasped and manipulated. As shown in FIG.

4A, the handle member 42 has a generally elongate shape, and it includes a proximal end 42a and a distal end 42b that is removably or fixedly coupled to the elongate needle 44. The handle member 42 can also include a suture-receiving channel (not shown) formed therein for seating the free end 30b of the suture 30 that extends from the second anchor body 20. The suture-receiving channel preferably extends from the distal end 42b of the handle 42 toward the proximal end 42a of the handle 42. While not illustrated, the handle 42 can also include an engagement mechanism adapted to releasably engage the suture 30 to securely retain the first anchor body 10 within the elongate needle 44 during deployment of the needle 44 through tissue.

As stated above, the handle member 42 can also include a trigger mechanism 46 formed thereon that, upon actuation, is effective to advance the first anchor body 10 in a distal direction. While a variety of trigger mechanisms can be used, in an exemplary embodiment the trigger mechanism 46 includes a pusher shaft (not shown) that is slidably disposed through the handle 42 and through at least a portion of the needle 44, and an actuating mechanism 50, such as a knob or button, that is mated to the pusher shaft, and that is slidably movable with respect to the handle 42. When the actuating mechanism 50 is moved in a distal direction with respect to the handle 42, it is effective to move the pusher shaft within the needle 44 in a distal direction, thereby pushing the first anchor body 10 distally to release the first anchor body 10. In use, the first anchor body 10 is loaded onto the delivery device 40 by placing the substantially cylindrical tissue-engaging portion 14 of the first anchor body 10 in the lumen 45 of the needle 44 with the central portion 12 extending through the channel 48, and sliding the first anchor body 10 proximally along the needle 44. The free end 30b of suture 30 is positioned toward the handle 42, preferably in the suture-receiving recess in the handle 42, such that the second anchor body 20 is positioned proximal to the first anchor body 10. Once the first and second anchor bodies 10, 20 are loaded onto the delivery device 40, the device 40 can be used to repair a tear.

Figure 5:
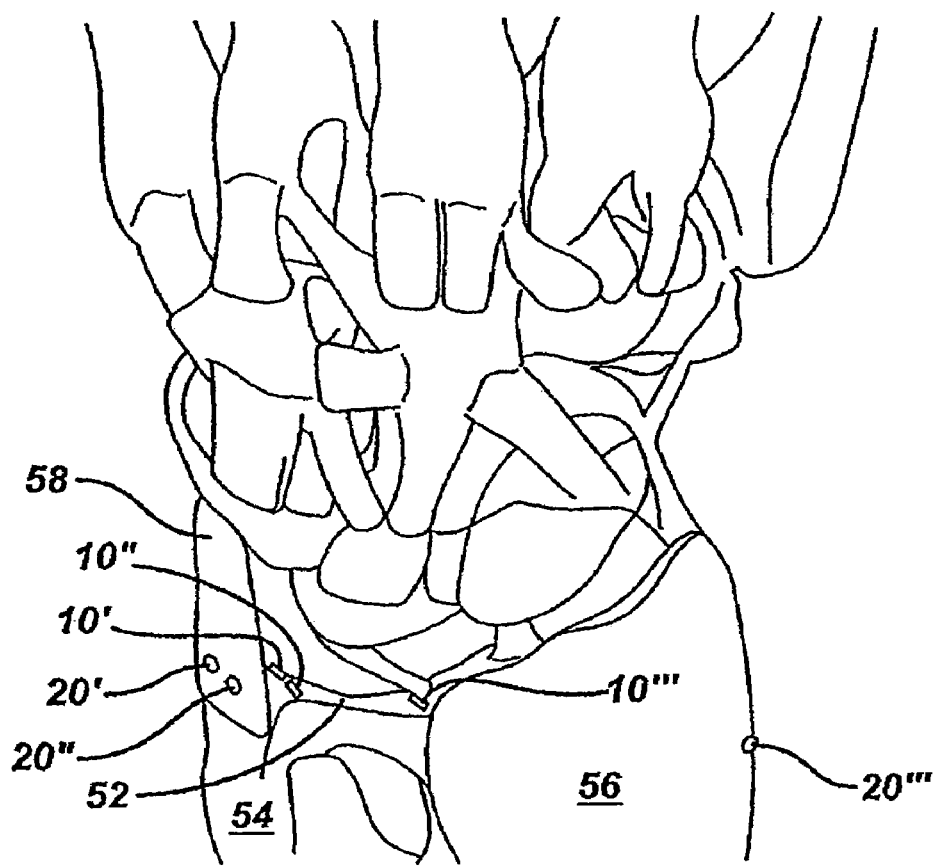
FIG. 5 is an illustration of a human wrist showing two anchoring systems, each including first and second anchor bodies, extending between an ulna side of the triangular fibrocartilage complex and the capsule of a the human wrist, and a third anchoring system, including first and second anchor bodies, extending between a radial side of the triangular fibrocartilage complex and the radius bone in accordance with another embodiment of the present invention.

While a person skilled in the art will appreciate that the device of the present invention can be used to repair a variety of torn tissue, the device is preferably used to repair a torn or damaged TFCC of a patient's wrist. FIG. 5 illustrates a human wrist which includes the triangular fibrocartilage complex (TFCC) 52, the ulna bone 54, the radial bone 56, and the dorsal capsule and extensor carpi ulnaris subsheath, collectively referred to as the capsule 58. The particular technique for repairing a torn TFCC will depending on the location of the tear, and tears can occur on both the radial and ulna side of the TFCC. FIG. 5, however, illustrates repairs of both ulna- and radial-sided tears.

One skilled in the art will appreciate that the system of the invention is used with known and accepted arthroscopic surgical techniques, including patient preparation, anesthetization, and creation of one or more portals through a patient's skin.

For ulna-sided tears, the elongate needle 44 of the delivery device 40 is inserted arthroscopically through a small incision in the skin (not shown), through the capsule 58 which serves as the anchoring tissue, and then through the torn TFCC 52 to positioned the first anchor body, e.g., anchor body 10', adjacent to the TFCC 52. The second anchor body, e.g., anchor body 20', is separated from the first anchor body 10' by a length of suture (not shown), and thus the second anchor body 20', which is not inserted through the capsule 58 or the TFCC 52, remains on the outer surface of the capsule 58. Accordingly, the first and second anchor bodies 10', 20' are positioned on opposed sides of the capsule 58 and the TFCC 52.

The first anchor body 10' can then be released by sliding the actuating mechanism 50 of the trigger 46 distally, and the delivery device 40 can be removed. The free end 30b of the suture 30 can then be tensioned to cause the first and second anchor bodies 10', 20' to be pulled toward one another, thereby pulling the torn TFCC 52 toward the capsule 58 to re-approximate the tear in the TFCC 52, as shown in FIG. 5. The free end 30b of the suture 30 can then be trimmed. Since a self-locking slip knot 32 is used, the first and second anchor bodies 10', 20' will be securely attached to one another with the capsule 58 and TFCC 52 therebetween, and additional knot tying procedures are not necessary. The procedure can be repeated to implant additional anchor systems as may be necessary. FIG. 5, for example, illustrates a second anchor system having first and second anchor bodies 10'', 20'' anchoring the TFCC 52 to the capsule 58.

Ulna-sided TFCC tears can also be repaired by anchoring the torn tissue 52 to the ulna 54, rather than to the capsule 58. Such a procedure follows the same steps recited above, however, rather than inserting the needle 44 through the capsule 58, it is inserted through a bone tunnel (not shown) formed in the ulna styloid 54.

For radial-sided tears, the elongate needle 44 of the delivery device 40 is inserted arthroscopically through a small incision in the skin (not shown), through the a bone tunnel (not shown) formed in the radius 56, which serves as the anchoring tissue, and then through the torn TFCC 52 to position the first anchor body, e.g., anchor body 10''', on the far side of the TFCC 52. The second anchor body, e.g., anchor body 20''', is separated from the first anchor body 10''' by a length of suture 30 (not shown), and thus the second anchor body 20''' is not inserted through the radius 56 or the TFCC 52, thereby positioning the first and second anchor bodies 10''', 20''' on opposed sides of the radius 56 and the TFCC 52. The first anchor body 10''' can then be released by sliding the actuating mechanism 50 of the trigger 46 distally, and the delivery device 40 can be removed. The free end 30b of the suture 30 can then be tensioned to cause the first and second anchor bodies 10''', 20''' to be pulled toward one another, thereby pulling the torn TFCC 52 toward the radius 56 to re-approximate the torn TFCC 52, as shown in FIG. 5. The free end 30b of the suture 30 can then be trimmed. Again, since a slip knot 52 is used, the first and second anchor bodies 10''', 20''' will be securely attached to one another with the radius 56 and TFCC 52 therebetween, and additional knot tying procedures are not necessary. The procedure can be repeated to implant additional anchor systems as may be necessary.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for repairing tears in the triangular fibrocartilage complex of a patient's wrist, comprising:
    passing a delivery device through an anchoring tissue and a portion of the triangular fibrocartilage complex of a patient's wrist, the delivery device carrying a first anchor body that is connected to a second anchor body by a suture;
    releasing the first anchor body from the delivery device such that the first anchor body is positioned across a torn portion of the triangular fibrocartilage complex, the second anchor body is positioned across an anchoring tissue, and the suture extends therebetween; and tensioning the suture to anchor the triangular fibrocartilage complex to the anchoring tissue.

2. The method of claim 1, wherein the triangular fibrocartilage complex has an ulna-sided tear, and the anchoring tissue is selected from the group consisting of the dorsal capsule and the extensor carpi ulnaris subsheath, and the ulna bone.

3. The method of claim 1, wherein the triangular fibrocartilage complex has a radial-sided tear, and the anchoring tissue comprises the radius bone.

4. The method of claim 1, wherein the suture includes a slip knot formed thereon, and wherein the step of tensioning the suture comprising pulling a trailing end of the suture such that the slip knot and the second anchor body move toward the first anchor body.

5. The method of claim 1, wherein each anchor body includes a central portion adapted to receive the suture, and a tissue-engaging portion.

6. The method of claim 5, wherein each anchor body includes a bore extending through the central portion for receiving the suture.

7. The method of claim 5, wherein the central portion of the first anchor body is substantially semi-circular, and the tissue-engaging portion is generally elongate.

8. The method of claim 7, wherein the central portion of the first anchor body is substantially planar, and the tissue-engaging portion is substantially cylindrical.

9. The method of claim 7, wherein the tissue-engaging portion has a length that is greater than a maximum diameter of the central portion such that opposed ends of the tissue-engaging portion form tissue-engaging wings.

10. The method of claim 7, wherein the tissue-engaging portion has a length that is greater than a height of the central portion.

11. The method of claim 5, wherein the tissue-engaging portion of the second anchor body is in the form of a circular base, and wherein the central portion comprises a substantially cylindrical extension of the circular base with chamfered sidewalls.

12. The method of claim 11, wherein the circular base and the substantially cylindrical extension further comprise a suture-receiving bore extending therethrough.

13. The method of claim 12, wherein the suture-receiving bore in the circular base further comprises a recess formed in an opening thereof, the recess being adapted to seat a knot formed on the suture.

14. The method of claim 13, wherein the recess is formed from a chamfer in the tissue-engaging portion.

15. The method of claim 11, wherein a diameter of the circular base is greater than a maximum diameter of the substantially cylindrical extension.

16. The method of claim 1, wherein the first and second anchor bodies are formed from a bioabsorbable polymeric material.

17. The method of claim 1, wherein the suture is selected from the group consisting of non-bioabsorbable, and bioabsorbable sutures.

18. The method of claim 1, wherein the delivery device includes an elongate needle having a channel formed in at least a distal portion thereof, wherein the channel adapted to slidably receive at least a portion of the first anchor body.

19. The method of claim 18, wherein the channel in the elongate needle is adapted to slidably receive a plurality of anchor bodies.

20. The method of claim 18, wherein the first anchor body includes a tissue-engaging portion that is adapted to be slidably received in the channel formed in the elongate needle of the delivery device.

21. The method of claim 18, wherein at least the distal-most portion of the delivery needle has a diameter in the range of about 16 to 18 gauge.

22. The method of claim 18, further comprising a handle member coupled to the elongate needle, and a trigger mechanism formed on the handle and effective to, upon actuation, advance the first anchor body in a distal direction to release the first anchor body.

23. The method of claim 18, further comprising a handle member coupled to the elongate needle and having a suture-receiving channel formed therein.

24. A method for repairing tears in the triangular fibrocartilage complex of a patient's wrist, comprising:

passing a delivery device through a portion of a torn triangular fibrocartilage complex of a patient's wrist at a first location, the delivery device carrying first and second anchor bodies that are connected to one another by a suture;

releasing the first anchor body from the delivery device such that the first anchor body is resting against an anchoring tissue;

passing the delivery device through a portion of the torn triangular fibrocartilage complex of a patient's wrist at a second location adjacent to the first location;

releasing the second anchor body from the delivery device such that the second anchor body is resting against the anchoring tissue adjacent to the first anchor body, and the suture extends from the first anchor body and second anchors bodies across the torn triangular fibrocartilage complex, and a portion of the suture rests against a tissue surface opposed to the anchoring tissue; and tensioning the suture to re-approximate the torn triangular fibrocartilage complex.

25. The method of claim 24, wherein the tissue surface that a portion of the suture rests against comprises the triangular fibrocartilage complex.

26. The method of claim 24, wherein the anchoring tissue is the triangular fibrocartilage complex, and the tissue surface that a portion of the suture rests against is selected from the group consisting of the dorsal capsule and the extensor carpi ulnaris subsheath, and the ulna bone.

27. The method of claim 24, wherein the anchoring tissue is the triangular fibrocartilage complex, and the tissue surface that a portion of the suture rests against comprises the radius bone.

* * * * *